United States Patent [19]

Baumann et al.

[11] Patent Number: 5,661,106

[45] Date of Patent: Aug. 26, 1997

[54] 3-(HET)ARYLOXY(THIO)CARBOXYLIC ACID DERIVATIVES, THEIR PREPARATION AND INTERMEDIATES FOR THEIR PREPARATION

[75] Inventors: Ernst Baumann, Dudenhofen; Joachim Rheinheimer; Uwe Josef Vogelbacher, both of Ludwigshafen; Matthias Bratz, Speyer; Norbert Meyer, Ladenburg; Matthias Gerber, Limburgerhof; Karl-Otto Westphalen, Speyer; Helmut Walter, Obrigheim; Wilhelm Rademacher, Limburgerhof, all of Germany

[73] Assignee: BASF Aktiengesellschaft, Ludwigshafen, Germany

[21] Appl. No.: 537,759

[22] PCT Filed: Apr. 14, 1994

[86] PCT No.: PCT/EP94/01156

§ 371 Date: Oct. 19, 1995

§ 102(e) Date: Oct. 19, 1995

[87] PCT Pub. No.: WO94/25443

PCT Pub. Date: Nov. 10, 1994

[30] Foreign Application Priority Data

Apr. 23, 1993 [DE] Germany .................. 43 13 413.0

[51] Int. Cl.$^6$ .................. H01N 43/54; C07D 239/60; C07D 239/52; C07D 333/24
[52] U.S. Cl. .................. 504/227; 504/239; 504/242; 504/243; 544/216; 544/217; 544/218; 544/219; 544/302; 544/314; 544/318; 544/319; 544/335
[58] Field of Search .................. 544/216, 217, 544/218, 219, 302, 314, 318, 319, 335; 504/227, 239, 242, 243

[56] References Cited

U.S. PATENT DOCUMENTS 5,270,289  12/1993  Harde et al. .................. 504/243

FOREIGN PATENT DOCUMENTS

| 98 892 | 1/1984 | European Pat. Off. . |
|---|---|---|
| 347 811 | 12/1989 | European Pat. Off. . |
| 400 741 | 12/1990 | European Pat. Off. . |
| 409 368 | 1/1991 | European Pat. Off. . |
| 415 384 | 3/1991 | European Pat. Off. . |
| 481 512 | 4/1992 | European Pat. Off. . |
| 517 215 | 12/1992 | European Pat. Off. . |
| 41 42 570 | 6/1993 | European Pat. Off. . |
| 3-228117 | 6/1993 | Japan . |

OTHER PUBLICATIONS

J. March, Advanced Organic Chem. 2nd ed, 1983, p. 862 and 750.
Japanese Abstracts JP 3193765 (1991).

28 Heterocycles, vol. 119, 1993, p. 883.

Direct Enantiomeric . . . , Nishi et al., Chromatographia, vol. 35, No. 5/6, Mar. 1993.

Aust J. Chem, 1992, 45, 1833–1843, Brown et al.

Synthesis and Antihypertensive . . . , Chem. Pharm. Bull. 40(8) 2055–2061 (1992).

Advanced Organic Chemistry, Third Ed., Jerry March p. 862 and 750 (1983).

*Primary Examiner*—Richard L. Raymond
*Attorney, Agent, or Firm*—Keil & Weinkauf

[57] ABSTRACT 3-(Het)aryloxy(thio)carboxylic acid derivatives of the formula I

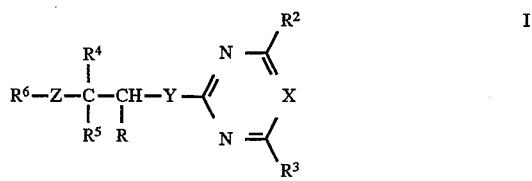

where

- $R^1$ is hydrogen, COOH or a radical which can be hydrolyzed to give COOH;
- $R^2$ and $R^3$ are each halogen, alkyl, haloalkyl, alkoxy, haloalkoxy or alkylthio;
- X is nitrogen or $CR^{14}$, where $R^{14}$ is hydrogen or, together with $R^3$, forms a 3-membered or 4-membered alkylene or alkenylene chain, in each of which a methylene group is replaced by oxygen;
- $R^4$ is alkyl, cycloalkyl, cycloalkenyl, alkenyl or alkynyl, each of which is unsubstituted or substituted;
   an unsubstituted or substituted five-membered or six-membered heteroaromatic structure containing one to three nitrogen atoms or one sulfur or oxygen atom; unsubstituted or substituted phenyl or naphthyl;
   $R^4$ and $R^5$, together with the neighboring carbon atom, form a 3-membered to 8-membered ring which may contain an oxygen or sulfur atom and which is unsubstituted or substituted;
- $R^5$ is hydrogen, alkyl, alkenyl, alkynyl, cycloalkyl, haloalkyl, alkoxyalkyl, alkylthioalkyl or phenyl, each of which is unsubstituted or substituted;
- $R^6$ is unsubstituted or substituted phenyl or naphthyl or an unsubstituted or substituted five-membered or six-membered heteroaromatic structure containing one to three nitrogen atoms or one sulfur or oxygen atom;
- Y is sulfur or oxygen or a single bond; and
- Z is sulfur or oxygen.

14 Claims, No Drawings

3-(HET)ARYLOXY(THIO)CARBOXYLIC ACID DERIVATIVES, THEIR PREPARATION AND INTERMEDIATES FOR THEIR PREPARATION

This application is a 371 of PCT/EP94/01156, filed Apr. 14, 1994.

The present invention relates to 3-(het)aryloxy(thio) carboxylic acid derivatives of the general formula I

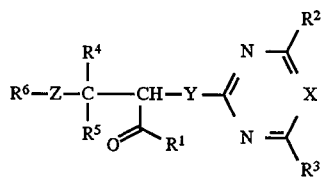

where $R^1$ is (a) hydrogen;

(b) a succinylimidoxy group;

(c) a 5-membered heteroaromatic structure which is bonded via a nitrogen atom, contains two or three nitrogen atoms and may carry one or two halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

(d) a radical

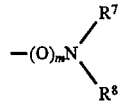

where m is 0 or 1 and $R^7$ and $R^8$, which may be identical or different, have the following meanings: hydrogen;

$C_1$–$C_8$-alkyl, $C_3$–$C_6$-alkenyl, $C_3$–$C_6$-alkynyl or $C_3$–$C_{12}$-cycloalkyl, where each of these radicals may carry one to five halogen atoms and/or one or two of the following groups:

$C_1$–$C_4$-alkoxy, $C_3$–$C_6$-alkenyloxy, $C_3$–$C_6$-alkynyloxy, $C_1$–$C_4$-alkylthio, $C_3$–$C_6$-alkenylthio, $C_3$–$C_6$-alkynylthio, $C_1$–$C_4$-haloalkoxy, $C_1$–$C_6$-alkylcarbonyl, $C_3$–$C_6$-alkenylcarbonyl, $C_3$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, di-$C_1$–$C_4$-alkylamino, cyclo-$C_1$–$C_6$-alkyl, phenyl or phenyl which is monosubstituted or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

phenyl which may be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

$R^7$ and $R^8$ together form a cyclic, optionally substituted $C_4$–$C_7$-alkylene chain or together form a cyclic, optionally substituted $C_3$–$C_6$-alkylene chain containing a heteroatom selected from the group consisting of oxygen, sulfur and nitrogen;

(e) $R^1$ is furthermore a group

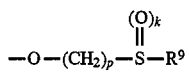

where $R^9$ is $C_1$–$C_4$-alkyl, phenyl or phenyl which is monosubstituted or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-akylthio [sic], or $C_1$–$C_4$-haloalkyl, $C_3$–$C_6$-alkenyl or $C_3$–$C_6$-alkynyl, p may be 1, 2, 3 or 4 and k may be 0, 1 or 2.

(f) a radical $OR^{10}$, where $R^{10}$ is:

i) hydrogen, an alkali metal cation, one equivalent of an alkaline earth metal cation, the ammonium cation or an organic ammonium ion;

ii) $C_3$–$C_{12}$-cycloalkyl which may carry one to three $C_1$–$C_4$-alkyl radicals;

iii) $C_1$–$C_{10}$-alkyl which may carry one to five halogen atoms and/or one of the following radicals:
$C_1$–$C_4$-alkoxy, $C_1$–$C_4$-alkylthio, cyano, $C_1$–$C_8$-alkylcarbonyl, $C_3$–$C_{12}$-cycloalkyl, $C_1$–$C_8$-alkoxycarbonyl, phenyl, phenoxy or phenylcarbonyl, where the aromatic radicals in turn may each carry one to five halogen atoms and/or one to three of the following radicals:
$C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

iv) $C_1$–$C_{10}$-alkyl which may carry one to five halogen atoms and carries one of the following radicals: a 5-membered heteroaromatic structure containing one to three nitrogen atoms or a 5-membered heteroaromatic structure containing one nitrogen atom and one oxygen or sulfur atom, each of its structures may carry one to four halogen atoms and/or one or two of the following radicals:
$C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

v) $C_2$–$C_6$-alkyl which carries one of the following radicals in the 2 position: $C_1$–$C_6$-alkoxyimino, $C_3$–$C_6$-alkenyloxyimino, $C_3$–$C_6$-haloalkenyloxyimino or benzyloxyimino;

vi) $C_3$–$C_6$-alkenyl or $C_3$–$C_6$-alkynyl, where these groups in turn may carry one to five halogen atoms;

vii) phenyl which may carry one to five halogen atoms and/or one to three of the following radicals:
$C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

viii) a 5-membered heteroaromatic structure which is bonded via a nitrogen atom, contains one to three nitrogen atoms and may carry one or two halogen atoms and/or one or two of the following radicals:
$C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

ix) a group

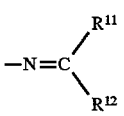

where $R^{11}$ and $R^{12}$ may be identical or different and are each:

$C_1$–$C_{10}$-alkyl, $C_3$–$C_6$-alkenyl, $C_3$–$C_6$-alkynyl or $C_3$–$C_7$-cycloalkyl, where these radicals may carry one $C_1-C_4$-alkoxy or $C_1-C_4$-alkylthio and/or one phenyl radical;

phenyl which may be substituted by one or more of the following radicals:

halogen, nitro, cyano, $C_1-C_4$-alkyl, $C_1-C_4$-haloalkyl, $C_1-C_4$-alkoxy, $C_1-C_4$-haloalkoxy or $C_1-C_4$-alkylthio;

or $R^{11}$ and $R^{12}$ together form a $C_3-C_{12}$-alkylene chain which may carry one to three $C_1-C_4$-alkyl groups;

(g) or $R^1$ forms a radical

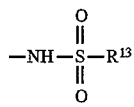

where $R^{13}$ is:

$C_1-C_4$-alkyl, $C_3-C_6$-alkenyl, $C_3-C_6$-alkynyl or $C_3-C_7$-cycloalkyl, where these radicals may carry one $C_1-C_4$-alkoxy or $C_1-C_4$-alkylthio and/or one phenyl radical;

phenyl which may be substituted by one to five halogen atoms and/or by one to three of the following radicals: halogen, nitro, cyano, $C_1-C_4$-alkyl, $C_1-C_4$-haloalkyl, $C_1-C_4$-alkoxy, $C_1-C_4$-haloalkoxy or $C_1-C_4$-alkylthio;

$R^2$ is halogen, $C_1-C_4$-alkyl, $C_1-C_4$-haloalkyl, $C_1-C_4$-alkoxy, $C_1-C_4$-haloalkoxy or $C_1-C_4$-alkylthio;

X is nitrogen or $CR^{14}$, where $R^{14}$ is hydrogen or, together with $R^3$, forms a 3-membered or 4-membered alkylene or alkenylene chain, in each of which a methylene group is replaced by oxygen;

$R^3$ is halogen, $C_1-C_4$-alkyl, $C_1-C_4$-haloalkyl, $C_1-C_4$-alkoxyl, $C_1-C_4$-haloalkoxy or $C_1-C_4$-alkylthio or $R^3$ is linked to $R^{14}$ as stated above to form a 5-membered or 6-membered ring;

$R^4$ is $C_1-C_{10}$-alkyl which may carry one to five halogen atoms and/or one of the following radicals: $C_1-C_4$-alkoxy, $C_1-C_4$-alkylthio, cyano, $C_1-C_8$-alkylcarbonyl, $C_1-C_8$-alkoxycarbonyl, phenyl, phenoxy or phenylcarbonyl, where the phenyl radicals in turn may carry one to five halogen atoms and/or one to three of the following radicals: $C_1-C_4$-alkyl, $C_1-C_4$-haloalkyl, $C_1-C_4$-alkoxy, $C_1-C_4$-haloalkoxy and/or $C_1-C_4$-alkylthio;

$C_1-C_{10}$-alkyl which may carry one to five halogen atoms and carries one of the following radicals: a five-membered heteroaromatic structure which contains one to three nitrogen atoms and/or one sulfur or oxygen atom and may carry one to four halogen atoms and/or one or two of the following radicals: $C_1-C_4$-alkyl, $C_1-C_4$-haloalkyl, $C_1-C_4$-alkoxy, $C_1-C_4$-haloalkoxy, $C_1-C_4$-alkylthio and/or phenyl;

a $C_3-C_{12}$-cycloalkyl or $C_3-C_{12}$-cycloalkenyl group which may contain one oxygen or sulfur atom and may carry one to five halogen atoms and/or one of the following radicals: $C_1-C_4$-alkyl, $C_1-C_4$-alkoxy, $C_1-C_4$-alkylthio, cyano, $C_1-C_8$-alkylcarbonyl, $C_1-C_8$-alkoxycarbonyl, phenyl, phenoxy or phenylcarbonyl, where the phenyl radicals in turn may carry one to five halogen atoms and/or one to three of the following radicals: $C_1-C_4$-alkyl, $C_1-C_4$-haloalkyl, $C_1-C_4$-alkoxy, $C_1-C_4$-haloalkoxy and/or $C_1-C_4$-alkylthio;

$C_3-C_6$-alkenyl or $C_3-C_6$-alkynyl, each of which may carry one to five halogen atoms and/or one of the following radicals: $C_1-C_4$-alkyl, $C_1-C_4$-alkoxy, $C_1-C_4$-alkylthio, cyano, $C_1-C_8$-alkylcarbonyl, $C_1-C_8$-alkoxycarbonyl, phenyl, phenoxy or phenylcarbonyl, where the phenyl radicals in turn may carry one to five halogen atoms and/or one to three of the following radicals: $C_1-C_4$-alkyl, $C_1-C_4$-haloalkyl, $C_1-C_4$-alkoxy, $C_1-C_4$-haloalkoxy and/or $C_1-C_4$-alkylthio;

a five-membered or six-membered heteroaromatic structure which contains one to three nitrogen atoms and/or one sulfur or oxygen atom and may carry one to four halogen atoms and/or one or two of the following radicals: $C_1-C_4$-alkyl, $C_1-C_4$-haloalkyl, $C_1-C_4$-alkoxy, $C_1-C_4$-haloalkoxy, $C_1-C_4$-alkylthio, phenyl, phenoxy or phenylcarbonyl, where the phenyl radicals in turn may carry one to five halogen atoms and/or one to three of the following radicals: $C_1-C_4$-alkyl, $C_1-C_4$-haloalkyl, $C_1-C_4$-alkoxy, $C_1-C_4$-haloalkoxy and/or $C_1-C_4$-alkylthio;

phenyl or naphthyl, each of which may be substituted by one or more of the following radicals: halogen, nitro, cyano, hydroxyl, $C_1-C_4$-alkyl, $C_1-C_4$-haloalkyl, $C_1-C_4$-alkoxy, $C_1-C_4$-haloalkoxy, phenoxy, $C_1-C_4$-alkylthio, amino, $C_1-C_4$-alkylamino or $C_1-C_4$-dialkylamino;

$R^4$ and $R^5$, together with the neighboring carbon atom, form a 3-membered to 8-membered ring which may contain one oxygen or sulfur atom and may carry one to three of the following radicals: $C_1-C_4$-alkyl, halogen, $C_1-C_4$-haloalkyl, $C_1-C_4$-alkoxy, $C_1-C_4$-haloalkoxy and/or $C_1-C_4$-alkylthio;

$R^5$ is hydrogen, $C_1-C_4$-alkyl, $C_3-C_6$-alkenyl, $C_3-C_6$-alkynyl, $C_3-C_7$-cycloalkyl, $C_1-C_4$-haloalkyl, $C_1-C_4$-alkoxyalkyl, $C_1-C_4$-alkylthioalkyl or phenyl or $R^5$ is linked to $R^4$ as stated above to form a 3-membered to 8-membered ring;

$R^6$ is phenyl or naphthyl, each of which may be substituted by one or more of the following radicals: halogen, nitro, cyano, hydroxyl, amino, $C_1-C_4$-alkyl, $C_1-C_4$-haloalkyl, $C_1-C_4$-alkoxy, $C_1-C_4$-haloalkoxy, phenoxy, $C_1-C_4$-alkylthio, $C_1-C_4$-alkylamino or $C_1-C_4$-dialkylamino;

a five-membered or six-membered heteroaromatic structure which contains one to three nitrogen atoms and/or one sulfur or oxygen atom and may carry one to four halogen atoms and/or one or two of the following radicals: $C_1-C_4$-alkyl, $C_1-C_4$-haloalkyl, $C_1-C_4$-alkoxy, $C_1-C_4$-haloalkoxy, $C_1-C_4$-alkylthio, phenyl, phenoxy or phenylcarbonyl, where the phenyl radicals in turn may carry one to five halogen atoms and/or one to three of the following radicals: $C_1-C_4$-alkyl, $C_1-C_4$-haloalkyl, $C_1-C_4$-alkoxy, $C_1-C_4$-haloalkoxy and/or $C_1-C_4$-alkylthio;

Y is sulfur or oxygen or a single bond; and

Z is sulfur or oxygen.

The prior art, e.g. EP-A 347 811, JP-A31 93 796, EP-A 400 741, EP-A 409 368, EP-A 481 512, EP-A 517 215, Chem. Abs. 119 (1993), 139254e and EP-A 548 710 describes similar carboxylic acid derivatives. 3-Alkoxy derivatives are also among the derivatives described, but not 3-(het)aryloxy(thio)carboxylic acid derivatives. The herbicidal and/or bioregulatory action and selectivity of the known compounds are, however, not always satisfactory.

It is an object of the present invention to provide compounds having improved selectivity and/or biological activity.

We have found that this object is achieved and that the 3-(het)aryloxy(thio)carboxylic acid derivatives defined at the outset have excellent herbicidal and plant growth-regulating properties. Furthermore, the compounds I have good pharmacological efficacy, particularly in the cardiovascular sector.

The preparation of the novel compounds starts from the epoxides IV, which are obtained in a generally known manner from the aldehydes or ketones II

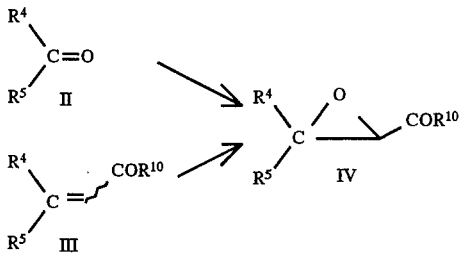

as described, for example, in J. March, Advanced Organic Chemistry, 2nd ed., 1983, page 862, or from the olefins III, as described, for example, in ibid., page 750.

3-(Het)aryloxy(thio)carboxylic acid derivatives of the general formula VI can be prepared by reacting the epoxide of the general formula IV with (het)arylthio or (het)aryloxy compounds of the general formula V, where $R^6$ and Z have the meanings stated in claim 1.

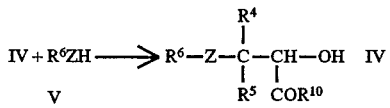

For this purpose, compounds of the general formula IV are heated with an excess of the compounds of the formula V, for example with from 1.2 to 7, preferably from 2 to 5, mole equivalents of V, to 50°–200° C., preferably 80°–150° C. The reaction can also be carried out in the presence of a diluent. All solvents which are inert to the reagents used may be employed for this purpose.

Examples of such solvents or diluents are water, aliphatic, alicyclic and aromatic hydrocarbons, each of which may be chlorinated, for example hexane, cyclohexane, petroleum ether, naphtha, benzene, toluene, xylene, methylene chloride, chloroform, carbon tetrachloride, ethylene chloride and trichloroethylene, ethers, such as diisopropyl ether, dibutyl ether, propylene oxide, dioxane and tetrahydrofuran, ketones, for example acetone, methyl ethyl ketone, methyl isopropyl ketone and methyl isobutyl ketone, nitriles, such as acetonitrile and propionitrile, alcohols, such as methanol, ethanol, isopropanol, butanol and ethylene glycol, esters, for example ethyl acetate and amyl acetate, amides, such as dimethylformamide and dimethylacetamide, sulfoxides and sulfones, for example dimethyl sulfoxide and sulfolane, and bases, such as pyridine.

If a solvent is used, the reaction is preferably carried out at from 0° C. to the boiling point of the solvent or solvent mixture.

The presence of a catalyst for the reaction may be advantageous. Suitable catalysts are acids and Lewis acids. Examples of these include sulfuric acid, hydrochloric acid, trifluoroacetic acid, boron trichloride etherate and titanium (IV) alcoholates.

The novel compounds in which Y is oxygen and the remaining substituents have the meanings stated under the general formula I can be prepared, for example, by reacting the 3-(het)aryloxy(thio)carboxylic acid derivatives of the general formula VI in which the substituents have the stated meanings with compounds of the general formula VII where $R^{15}$ is halogen or $R^{16}$—$SO_2$— and $R^{16}$ may be $C_1$–$C_4$-alkyl, $C_1$–$C_4$-haloalkyl or phenyl:

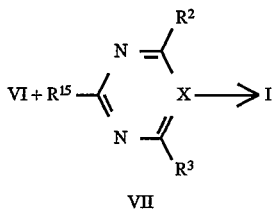

The reaction is preferably carried out in one of the above-mentioned inert diluents with the addition of a suitable base at from room temperature to the boiling point of the solvent.

The bases may be an alkali metal or alkaline earth metal hydride, such as sodium hydride, potassium hydride or calcium hydride, a carbonate, such as sodium carbonate or potassium carbonate, a metal hydroxide, such as sodium hydroxide or potassium hydroxide, or an organometallic compound, such as butyllithium, or an alkali metal amide, such as lithium diisopropylamide.

The novel compounds in which Y is sulfur and the remaining substituents have the meanings stated under the general formula I can be prepared, for example, by reacting 3-(het)aryloxy(thio)carboxylic acid derivatives of the general formula VIII, which are obtainable in a known manner from compounds of the general formula VI and in which the substituents have the abovementioned meanings, with compounds of the general formula IX where $R^2$, $R^3$ and X have the meanings stated under the general formula I.

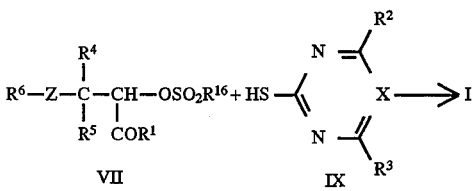

The reaction is preferably carried out in one of the above-mentioned inert diluents with the addition of a suitable base at from room temperature to the boiling point of the solvent.

The bases used may be organic bases, such as triethylamine, pyridine, imidazole or diazabicycloundecene, in addition to the abovementioned bases.

Compounds of the formula I can also be prepared by starting from the corresponding carboxylic acids, i.e. compounds of the formula I in which $R^1$ is hydroxyl, and first converting these in a conventional manner into an activated form, such as a halide, an anhydride or an imidazolide, and then reacting this with a corresponding hydroxyl compound $HOR^{10}$. This reaction can be carried out in the conventional solvents and often requires the addition of a base, the abovementioned bases being suitable. These two steps can also be simplified, for example, by allowing the carboxylic acid to act on the hydroxy compound in the presence of a water-eliminating agent, such as a carbodiimide.

In addition, compounds of the formula I can also be prepared by starting from the salts of the corresponding carboxylic acids, i.e. from compounds of the formula I in which $R^1$ is OM, where M may be an alkali metal cation or one equivalent of an alkaline earth metal cation. These salts can be reacted with many compounds of the formula $R^1$-A, where A is a conventional nucleonic leaving group, for example halogen, such as chlorine, bromine or iodine, or aryl- or alkylsulfonyl which is unsubstituted or substituted by halogen, alkyl or haloalkyl, e.g. toluenesulfonyl and methylsulfonyl, or another equivalent leaving group. Compounds of the formula $R^1$-A having a reactive substituent A are known or can be readily obtained on the basis of general technical knowledge. The reaction can be carried out in the conventional solvents and once again often requires the addition of a base, the abovementioned bases being suitable.

With regard to the biological activity, preferred 3-(het) aryloxy(thio)carboxylic acid derivatives are those of the general formula I in which the substituents have the following meanings:

$R^1$ is hydrogen,
a succinylimidoxy group;
a 5-membered heteroaromatic structure which is bonded via a nitrogen atom, such as pyrrolyl, pyrazolyl, imidazolyl or triazolyl, and which may carry one or two halogen atoms, in particular fluorine or chlorine and/or one or two of the following radicals: $C_1$–$C_4$-alkyl, such as methyl, ethyl, 1-propyl, 2-propyl, 2-methyl-2-propyl, 2-methyl-1-propyl, 1-butyl or 2-butyl; $C_1$–$C_4$-haloalkyl, in particular $C_1$- or $C_2$-haloalkyl, for example fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trifluoroethyl or pentafluoroethyl;

$C_1$–$C_4$-haloalkoxy, in particular $C_1$- or $C_2$-haloalkoxy, such as difluoromethoxy, trifluoromethoxy, chlorodifluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy, ethoxy or 1-methylethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio or ethylthio;

$R^1$ is furthermore a radical

where m is 0 or 1 and $R^7$ and $R^8$ may be identical or different and have the following meanings:
hydrogen;
$C_1$–$C_8$-alkyl, in particular $C_1$–$C_4$-alkyl as tested above;
$C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-3-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl, 2-butenyl, 3-methyl-2-butenyl or 3-methyl-2-pentenyl;

$C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl, 2-butynyl, 1-methyl-2-propynyl or 1-methyl-2-butynyl, in particular 2-propynyl;

$C_3$–$C_{12}$-cycloalkyl, in particular $C_3$–$C_7$-cycloalkyl, such as cyclopropyl, cyclobutyl, cyclopentyl, cyclohexyl or cycloheptyl, where these alkyl, cycloalkyl, alkenyl and alkynyl groups may each carry one to five halogen atoms, in particular fluorine or chlorine, and/or one or two of the following groups:

$C_1$–$C_4$-alkyl, $C_1$–$C_4$-alkoxy, $C_1$–$C_4$-alkylthio, $C_1$–$C_4$-haloalkoxy as stated above, $C_3$–$C_6$-alkenyloxy, $C_3$–$C_6$-alkenylthio, $C_3$–$C_6$-alkynyloxy, or $C_3$–$C_6$-alkynylthio, where the alkenyl and alkynyl moieties present in these radicals preferably have the above-mentioned meanings;

$C_1$–$C_6$-alkylcarbonyl, in particular methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, 1-hexylcarbonyl, 1-methylpentylcarbonyl, 2-methylpentylcarbonyl, 3-methylpentylcarbonyl, 4-methylpentylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,1,2-trimethylpropylcarbonyl, 1-ethyl-1-methylpropylcarbonyl or 1-ethyl-2-methylpropylcarbonyl;

$C_1$–$C_6$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, 1-pentyloxycarbonyl, 1-methylbutoxycarbonyl, 2-methylbutoxycarbonyl, 3-methylbutoxycarbonyl, 1,2-dimethylpropoxycarbonyl, 1,1-dimethylpropoxycarbonyl, 2,2-dimethylpropoxycarbonyl, 1-ethylpropoxycarbonyl, 1-hexyloxycarbonyl, 1-methylpentyloxycarbonyl, 2-methylpentyloxycarbonyl, 3-methylpentyloxycarbonyl, 4-methylpentyloxycarbonyl, 1,2-dimethylbutoxycarbonyl, 1,3-dimethylbutoxycarbonyl, 2,3-dimethylbutoxycarbonyl, 1,1-dimethylbutoxycarbonyl, 2,2-dimethylbutoxycarbonyl, 3,3-dimethylbutoxycarbonyl, 1,1,2-trimethylpropoxycarbonyl, 1,2,2-trimethylpropoxycarbonyl, 1-ethylbutoxycarbonyl, 2-ethylbutoxycarbonyl, 1-ethyl-2-methylpropoxycarbonyl, 1-heptyloxycarbonyl, 1-methylhexyloxycarbonyl, 2-methylhexyloxycarbonyl, 3-methylhexyloxycarbonyl, 4-methylhexyloxycarbonyl, 5-methylhexyloxycarbonyl, 1-ethylpentyloxycarbonyl, 2-ethylpentyloxycarbonyl, 1-propylbutoxycarbonyl or octyloxycarbonyl, in particular methoxycarbonyl, ethoxycarbonyl, 1-methylethoxycarbonyl or 1-methylpropoxycarbonyl;

$C_3$–$C_6$-alkenylcarbonyl, $C_3$–$C_6$-alkynylcarbonyl, $C_3$–$C_6$-alkenyloxycarbonyl or $C_3$–$C_6$-alkynyloxycarbonyl, where the alkenyl and alkynyl radicals are preferably defined as stated individually above;

phenyl, unsubstituted or monosubstituted or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, for example 2-fluorophenyl, 3-chlorophenyl, 4-bromophenyl, 2-methylphenyl, 3-nitrophenyl, 4-cyanophenyl, 2-trifluoromethylphenyl, 3-methoxyphenyl, 4-trifluoroethoryphenyl, 2-methylthiophenyl, 2,4-dichlorophenyl, 2-methoxy-3-methylphenyl, 2,4-dimethoxyphenyl, 2-nitro-5-cyanophenyl or 2,6-difluorophenyl;

di-$C_1$–$C_4$-alkylamino, in particular dimethylamino, dipropylamino, N-propyl-N-methylamino, N-propyl-N-ethylamino, diisopropylamino, N-isopropyl-N-methylamino, N-isopropyl-N-ethylamino or N-isopropyl-N-propylamino;

$R^7$ and $R^8$ are each furthermore phenyl, which may be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio as stated in particular above, or $R^7$ and $R^8$ together form a cyclic, optionally substituted $C_4$–$C_7$-alkylene chain which may contain a heteroatom selected from the group consisting of oxygen, sulfur and nitrogen, such as —(CH$_2$)$_4$—, —(CH$_2$)$_5$—, —(CH$_2$)$_6$—, —(CH$_2$)$_7$—, —(CH$_2$)$_2$—O—(CH$_2$)$_2$—, —CH$_2$—S—(CH$_2$)$_3$—, —(CH$_2$)$_2$—O—(CH$_2$)$_3$—, —NH—(CH$_2$)$_3$—, —CH$_2$—NH—(CH$_2$)$_2$—, —CH$_2$—CH=CH—CH$_2$— or —CH=CH—(CH$_2$)$_3$—;

$R^1$ is furthermore a group

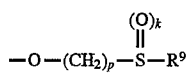

where k may be 0, 1 or 2, p may be 1, 2, 3 or 4 and $R^9$ is $C_1$–$C_4$-alkyl, $C_1$–$C_4$-haloalkyl, $C_3$–$C_6$-alkenyl, $C_3$–$C_6$-alkynyl or unsubstituted or substituted phenyl, as stated in particular above.

$R^1$ is furthermore a radical $OR^{10}$, where $R^{10}$ is:
  hydrogen, the cation of an alkali metal or the cation of an alkaline earth metal, such as lithium, sodium, potassium, calcium, magnesium or barium, or an environmentally compatible organic ammonium ion, such as tert-alkylammonium with up to 20 carbon atoms or ammonium [$NH_4^\oplus$];

$C_3$–$C_{12}$-cycloalkyl, in particular $C_3$–$C_7$-cycloalkyl as stated above, which may carry one to three $C_1$–$C_4$-alkyl groups;

$C_1$–$C_{10}$-alkyl, in particular methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,2-dimethylpropyl, 1,1-dimethylpropyl, 2,2-dimethylpropyl, 1-ethylpropyl, hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, heptyl, 1-methylhexyl, 2-methylhexyl, 3-methylhexyl, 4-methylhexyl, 5-methylhexyl, 1-ethylpentyl, 2-ethylpentyl, 1-propylbutyl or octyl, which may carry one to five halogen atoms, in particular fluorine or chlorine, and/or one of the following radicals:
    $C_1$–$C_4$-alkoxy, $C_1$–$C_4$-alkylthio, cyano, $C_1$–$C_8$-alkylcarbonyl, $C_3$–$C_{12}$-cycloalkyl [sic], $C_1$–$C_8$-alkoxycarbonyl, phenyl, phenoxy or phenylcarbonyl, where the aromatic radicals in turn may each carry one to five halogen atoms and/or one to three of the following radicals:
      $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

$C_1$–$C_{10}$-alkyl as stated above, which may carry one to five halogen atoms, in particular fluorine and/or chlorine, and carries one of the following radicals: a 5-membered hetero-aromatic structure which contains one to three nitrogen atoms, or one nitrogen atom and one oxygen or sulfur atom and which may carry one to four halogen atoms and/or one or two of the following radicals:
    $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. Particular examples are: 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl, 3-isopropylisoxazol-5-yl, 3-methylisoxazol-5-yl, oxazol-2-yl, thiazol-2-yl, imidazol-2-yl, 3-ethylisoxazol-5-yl, 3-phenylisoxazol-5-yl, 3-tert-butylisoxazol-5-yl;

$C_2$–$C_6$-alkyl which carries one of the following radicals in the 2 position: $C_1$–$C_6$-alkoxyimino, $C_3$–$C_6$-alkynyloxyimino, $C_3$–$C_6$-haloalkenyloxyimino or benzyloxyimino;

$C_3$–$C_6$-alkenyl or $C_3$–$C_6$-alkynyl, where these groups in turn may carry one to five halogen atoms;

$R^{10}$ is furthermore phenyl which may carry one to five halogen atoms and/or one to three of the following radicals:

$C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;

a 5-membered heteroaromatic structure which is bonded via a nitrogen atom, contains one to three nitrogen atoms and may carry one or two hydrogen atoms and/or one or two of the following radicals: $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. Particular examples are 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2,4-triazol-1-yl, 5-methyl-1,2,4-triazol-1-yl, 1-benzotriazolyl and 3,4-dichloroimidazol-1-yl;

$R^{10}$ is furthermore a group

where $R^{11}$ and $R^{12}$ may be identical or different and are each:
$C_1$–$C_{10}$-alkyl, $C_3$–$C_6$-alkenyl, $C_3$–$C_6$-alkynyl or $C_3$–$C_7$-cycloalkyl, where these radicals may carry $C_1$–$C_4$-alkoxy, $C_1$–$C_4$-alkylthio and/or unsubstituted or substituted phenyl, as stated in particular above;

phenyl, which may be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, where these radicals correspond in particular to the abovementioned ones;

or $R^{11}$ and $R^{12}$ together form a $C_3$–$C_{12}$-alkylene chain which may carry one to three $C_1$–$C_4$-alkyl groups and may contain a heteroatom selected from the group consisting of oxygen, sulfur and nitrogen, as stated in particular for $R^7$ and $R^8$;

$R^1$ is furthermore a radical

where $R^{13}$ is:
$C_1$–$C_4$-alkyl, $C_3$–$C_6$-alkenyl, $C_3$–$C_6$-alkynyl, $C_3$–$C_7$-cycloalkyl as stated in particular above, where these radicals may carry $C_1$–$C_4$-alkoxy, $C_1$–$C_4$-alkylthio and/or phenyl as stated above;

phenyl, unsubstituted or substituted, in particular as stated above;

$R^2$ is one of the alkyl, haloalkyl, alkoxy, haloalkoxy or alkylthio groups stated individually in the case of $R^1$ or is halogen, in particular chlorine, methyl, methoxy, ethoxy, difluoromethoxy or trifluoromethoxy;

X is nitrogen or $CR^{14}$, where $R^{14}$ is hydrogen or, together with $R^3$, forms a 4-membered or 5-membered alkylene or alkenylene chain, in each of which a methylene group is replaced by oxygen, such as —$CH_2$—$CH_2$—O—, —CH=CH—O—, —$CH_2$—$CH_2$—$CH_2$—O— or —CH=CH—$CH_2$—O—, in particular hydrogen or —$CH_2$—$CH_2$—O—;

$R^3$ is one of the $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio groups stated in the case of $R^1$ or is halogen, in particular chlorine, methyl, methoxy, ethoxy, difluoromethoxy or trifluoromethoxy; or is bonded to $R^6$ as stated above to form a 5-membered or 6-membered ring;

$R^4$ is $C_1$–$C_{10}$-alkyl as stated individually in the case of $R^1$, which may carry one to five halogen atoms, such as fluorine, chlorine, bromine or iodine, in particular fluorine or chlorine, and/or one of the following radicals: alkoxy, alkylthio, cyano, alkylcarbonyl, alkoxycarbonyl, phenyl, phenoxy or phenylcarbonyl as stated in general and in particular in the case of $R^1$;

$C_1$–$C_{10}$-alkyl as stated above, which may carry one to five halogen atoms as stated above, in particular fluorine or chlorine, and carries an unsubstituted or substituted 5-membered heteraromatic structure as stated above for $R^1$;

$C_3$–$C_{12}$-cycloalkyl, in particular $C_3$–$C_7$-cycloalkyl, or $C_3$–$C_{12}$-cycloalkenyl, in particular $C_4$–$C_7$-cycloalkenyl, where a methylene group in the saturated or unsaturated ring may be replaced by an oxygen or sulfur atom, such as cyclopropyl, cyclobutyl, cyclopentyl, cyclohexyl, cycloheptyl, tetrahydrofuranyl, tetrahydrothienyl, tetrahydropyranyl, tetrahydrothiopyranyl, cyclopropenyl, dihydrofuranyl, dihydrothienyl, dihydropyranyl or dihydrothiopyranyl, where the cycloalkyl or cycloalkenyl radicals may be substituted by one to five halogen atoms as stated above, in particular fluorine or chlorine and/or by one of the following radicals: $C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl as stated in general and in particular above;

$C_3$–$C_6$-alkenyl or $C_3$–$C_6$-alkynyl as stated in the case of $R^1$, which may carry one to five halogen atoms as stated above, in particular fluorine or chlorine, and/or one of the following radicals:

$C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl as stated in general and in particular above;

$R^4$ is furthermore 5-membered or 6-membered heteroaryl, such as furyl, thienyl, pyrryl, pyrazolyl, imidazolyl, triazolyl, isoxazolyl, oxazolyl, isothiazolyl, thiazolyl, thiadiazolyl, pyridyl, pyrimidinyl, pyrazinyl, pyridazinyl, triazinyl, for example 2-furanyl, 3-furanyl, 2-thienyl, 3-thienyl, 3-isoxazolyl, 4-isoxazolyl, 5-isoxazolyl, 3-isothiazolyl, 4-isothiazolyl, 5-isothiazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 2-pyrrolyl, 3-pyrrolyl, 3-pyrrolyl, [sic] 3-pyrazolyl, 4-pyrazolyl, 5-pyrazolyl, 2-pyridyl, 3-pyridyl, 4-pyridyl, oxa-2,4-diazolyl, oxa-3,4-diazoylyl, thia-2,4-diazolyl, thia-3,4-diazolyl, oxa-3,4-diazolyl, thia-2,4-diazolyl, thia-3,4-diazolyl [sic] or triazolyl, where the heteroaromatic structures may carry one to five halogen atoms as stated above, in particular fluorine or chlorine and/or one of the following radicals:

$C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl as stated in general and in particular above;

$R^4$ is furthermore phenyl or naphthyl, each of which may be substituted by one or more of the following radicals: halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, amino, $C_1$–$C_4$-alkylamino or $C_1$–$C_4$-dialkylamino, in particular as stated in the case of $R^7$ and $R^8$ or 3-hydroxyphenyl, 4-dimethylaminophenyl, 1-naphthyl, 2-naphthyl, 3-bromo-2-naphthyl, 4-methyl-1-naphthyl, 5-methoxy-1-naphthyl, 6-trifluoromethyl-1-naphthyl, 7-chloro-1-naphthyl or 8-hydroxy-1-naphthyl;

or $R^4$ and $R^5$, together with the neighboring carbon atom, form a 3-membered to 6-membered ring which may contain an oxygen or sulfur atom and is unsubstituted or, depending on the ring size, carries one to three of the following radicals:

$C_1$–$C_4$-alkyl, $C_1$–$C_4$-alkoxy, $C_1$–$C_4$-haloalkyl, $C_1$–$C_4$-haloalkoxy or $C_1$–$C_4$-alkylthio as stated in general and in particular above;

$R^5$ is hydrogen, $C_1$–$C_4$-alkyl, $C_3$–$C_6$-alkenyl, $C_3$–$C_6$-alkynyl, $C_3$–$C_7$-cycloalkyl, $C_1$–$C_4$-haloalkyl, $C_1$–$C_4$-alkoxyalkyl, $C_1$–$C_4$-alkylthioalkyl or phenyl, or $R^5$, together with $R^4$, forms a 3-membered to 6-membered ring as stated above;

$R^6$ is phenyl or naphthyl, which may be substituted by one or more of the following radicals: halogen, nitro, cyano, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, $C_1$–$C_4$-alkylamino or $C_1$–$C_4$-dialkylamino, as stated in particular in the case of $R^7$ and $R^4$;

a five-membered or six-membered heteroaromatic structure which contains one to three nitrogen atoms and/or one sulfur or oxygen atom and may carry one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl, phenoxy or phenylcarbonyl, where the phenyl radicals in turn may carry one to five halogen atoms and/or one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, as stated in particular in the case of $R^4$;

Y is sulfur, oxygen or a single bond and

Z is sulfur or oxygen.

Compounds of the formula I where $R^2$ and $R^3$ are each methoxy and X is CH are particularly preferred. Compounds of the formula I where $R^2$ and $R^3$ are each methoxy, X is CH, Y and Z are each oxygen and $R^5$ is $C_1$–$C_4$-alkyl are also preferred. A preferred radical in the case of $R^1$ is the group $OR^{10}$, where $R^{10}$ is hydrogen or $C_1$–$C_4$-alkyl.

$R^4$ is particularly preferably $C_1$–$C_4$-alkyl, unsubstituted or substituted phenyl or an aromatic heterocyclic radical containing a heteroatom, such as furyl or thienyl.

$R^6$ is particularly preferably phenyl, unsubstituted or monosubstituted to trisubstituted by halogen, $C_1$–$C_4$-alkyl and/or nitro.

Examples of preferred compounds are shown in the table below.

TABLE

| $R^1$ | $R^4$ | $R^5$ | $R^6$ | $R^2$ | $R^3$ | X | Y | Z |
|---|---|---|---|---|---|---|---|---|
| $OCH_3$ | Phenyl | $CH_3$ | Phenyl | $OCH_3$ | $OCH_3$ | CH | O | O |
| OH | Phenyl | $CH_3$ | Phenyl | $OCH_3$ | $OCH_3$ | CH | O | O |
| OH | Phenyl | $CH_3$ | Phenyl | $OCH_3$ | —O—$CH_2$—$CH_2$— | O | O | |
| OH | Phenyl | $CH_3$ | Phenyl | $OCH_3$ | $OCH_3$ | N | O | O |
| OH | Phenyl | $CH_3$ | Phenyl | $OCH_3$ | $OCH_3$ | CH | S | O |
| OH | Phenyl | $CH_3$ | Phenyl | $OCH_3$ | $OCH_3$ | CH | S | S |
| OH | Phenyl | $CH_3$ | Phenyl | $OCH_3$ | $OCH_3$ | CH | O | S |
| OH | Phenyl | H | Phenyl | $OCH_3$ | $OCH_3$ | CH | O | O |
| OH | Phenyl | i-Propyl | Phenyl | $OCH_3$ | $OCH_3$ | CH | O | O |
| OH | $CH_3$ | $CH_3$ | Phenyl | $OCH_3$ | $OCH_3$ | CH | O | O |
| OH | —($CH_2)_5$— | | Phenyl | Phenyl | $OCH_3$ | CH | O | O |
| OH | Phenyl | $CH_3$ | 2-Thiazolyl | $OCH_3$ | $OCH_3$ | CH | O | O |
| OH | 2-Thienyl | $CH_3$ | Phenyl | $OCH_3$ | $OCH_3$ | CH | O | O |
| $OCH_3$ | 2-Fluorophenyl | Ethyl | Phenyl | $OCH_3$ | $OCH_3$ | CH | O | O |
| $OC_2H_5$ | 3-Chlorophenyl | Propyl | Phenyl | $OCH_3$ | $OCH_3$ | N | O | O |
| $ON(CH_3)_2$ | 4-Bromophenyl | i-Propyl | Phenyl | $CF_3$ | $CF_3$ | CH | S | O |
| $ON=C(CH_3)_2$ | 2-Thienyl | Methyl | Phenyl | $OCF_3$ | $OCF_3$ | CH | O | S |
| NH—$SO_2$—$C_6H_5$ | 3-Thienyl | Methyl | Phenyl | $CH_3$ | $CH_3$ | CH | O | O |
| NHPhenyl | 2-Furyl | Methyl | Phenyl | Cl | Cl | CH | O | O |
| ONa | 3-Furyl | Methyl | Phenyl | $OCH_3$ | —O—$CH_2$—$CH_2$— | S | O | |
| O—$CH_2$≡CH | Phenyl | Ethyl | 2-Fluorophenyl | $OCH_3$ | $CF_3$ | CH | O | O |
| OH | Phenyl | Propyl | 3-Chlorophenyl | $OCH_3$ | $OCF_3$ | CH | O | S |
| $OCH_3$ | Phenyl | i-Propyl | 4-Bromophenyl | $OCH_3$ | $CH_3$ | CH | O | O |
| $OC_2H_5$ | Phenyl | Methyl | 4-Thiazolyl | $OCH_3$ | Cl | CH | S | O |
| $ON(CH_3)_2$ | 2-Methylphenyl | Methyl | Phenyl | $OCH_3$ | $OCH_3$ | CH | O | O |
| $ON=C(CH_3)_2$ | 3-Methoxyphenyl | Methyl | Phenyl | $OCH_3$ | $OCH_3$ | CH | O | O |
| NH—SO—$C_6H_5$ | 4-Nitrophenyl | Methyl | Phenyl | $OCH_3$ | $OCH_3$ | CH | O | O |
| NHPheynl | Methyl | Methyl | Phenyl | $CF_3$ | $CF_3$ | N | S | O |
| ONa | Methyl | Methyl | 2-Methylphenyl | $OCF_3$ | $OCF_3$ | N | O | S |
| O—$CH_2$—C≡CH | Methyl | Methyl | 3-Methoxyphenyl | $CH_3$ | $CH_3$ | N | O | O |
| OH | Methyl | Methyl | 4-Nitrophenyl | Cl | Cl | N | O | O |
| $OCH_3$ | Phenyl | Methyl | 3-Imidazolyl | $OCH_3$ | —O—$CH_2$—$CH_2$— | O | O | |
| $OC_2H_5$ | Pheynl | Methyl | 4-Imidazolyl | $OCH_3$ | $CF_3$ | N | S | O |
| $ON(CH_3)_2$ | Phenyl | Methyl | 2-Pyrazolyl | $OCH_3$ | $OCF_3$ | N | O | S |
| $ON=C(CH_3)_2$ | 2-Hydroxyphenyl | Methyl | Phenyl | $OCH_3$ | $CH_3$ | N | O | O |

TABLE-continued

| R¹ | R⁴ | R⁵ | R⁶ | R² | R³ | X | Y | Z |
|---|---|---|---|---|---|---|---|---|
| NH—SO₂—C₆H₅ | 3-Trifluoro-methylphenyl | Methyl | Phenyl | OCH₃ | Cl | N | O | O |
| NHPhenyl | 4-Dimethylamino-phenyl | Methyl | Phenyl | OCH₃ | OCH₃ | CH | S | O |
| ONa | 3-Imidazolyl | Ethyl | Phenyl | OCH₃ | OCH₃ | CH | S | S |
| O—CH₂—C≡CH | 4-Imidazolyl | Propyl | Phenyl | OCH₃ | OCH₃ | N | S | S |
| OH | 3-Pyrazolyl | i-Propyl | Phenyl | CF₃ | CF₃ | CH | O | S |
| OCH₃ | 4-Pyrazolyl | Methyl | Phenyl | OCF₃ | OCF₃ | CH | O | O |
| OC₂H₅ | Phenyl | Methyl | 2-Dimethyl-aminophenyl | CH₃ | CH₃ | CH | O | O |
| ON(CH₃)₂ | Phenyl | Methyl | 3-Hyroxyphenyl | Cl | Cl | CH | O | O |
| ON=C(CH₃)₂ | Phenyl | Methyl | 4-Trifluoro-methylphenyl | OCH₃ | —O—CH₂—CH₂— | | S | O |
| NH—SO₂—C₆H₅ | Phenyl | Methyl | 2-Oxazolyl | OCH₃ | CF₃ | N | S | S |
| NH-Phenyl | 2-Pyridyl | Methyl | 4-Isoxazolyl | OCH₃ | OCF₃ | N | S | S |
| ONa | 3-Pyridyl | Methyl | Phenyl | OCH₃ | CH₃ | N | O | O |
| O—CH₂—C≡CH | 4-Pyridyl | Methyl | Phenyl | OCH₃ | Cl | N | O | O |

The compounds I and the herbicides containing them and their environmentally compatible salts, for example of alkali metals and alkaline earth metals, ensure very good control of weeds in crops such as wheat, rice, corn, soybean and cotton, without damaging the crops, an effect which occurs in particular at low application rates. They may be applied, for example, in the form of directly sprayable aqueous solutions, powders, suspensions, including concentrated aqueous, oily or other suspensions or dispersions, emulsions, oil dispersions, pastes, dusting agents, broadcasting agents or granules, by spraying, nebulizing, dusting, broadcasting or pouring. The application forms depend on the intended uses; they should in any case ensure a very fine distribution of the novel active ingredients.

The compounds I are suitable in general for the preparation of directly sprayable solutions, emulsions, pastes or oil dispersions. Suitable inert additives include mineral oil fractions having a medium to high boiling point, such as kerosine or diesel oil, and coal tar oils and oils of vegetable or animal origin, aliphatic, cyclic and aromatic hydrocarbons, e.g. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersable granules by adding water. For the preparation of emulsions, pastes or oil dispersions, the substrates [sic] as such are dissolved in an oil or solvent, can be homogenized in water by means of wetting agents, adherents, dispersants or emulsifiers. However, it is also possible to prepare concentrates which consist of active ingredient, wetting agents, adherents, dispersants or emulsifiers and possibly solvents or oil and which are suitable for dilution with water.

Suitable surfactants are alkali metal, alkaline earth metal and ammonium salts of aromatic sulfonic acids, for example lignin-sulfonic, phenolsulfonic, naphthalenesulfonic and dibutylnaphthalenesulfonic acid, and of fatty acids, alkanesulfonates, alkylarylsulfonates, alkylsulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of naphthalene sulfonic acids with phenol and formaldehyde, polyoxyethylene octylphenyl ether, ethoxylated isooctyl-, octyl- or nonylphenyl, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene [lacuna], lauryl alcohol polyglycol ether acetate, sorbitol esters, lignin sulfite waste liquors or methyl cellulose.

Powders, broadcasting agents and dusting agents can be prepared by mixing or milling the active ingredients together with a solid carrier.

Granules, for example coated, impregnated and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders and other solid carriers.

The formulations contain in general from 0.01 to 95, preferably from 0.5 to 90%, by weight of active ingredient. The active ingredients are used in the purity of from 90 to 100%, preferably from 95 to 100% (according to the NMR spectrum).

Examples of formulations are:

I. 20 parts by weight of compound No. 2.2 are dissolved in a mixture which consists of 80 parts by weight of alkylated benzene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

II. 20 parts by weight of compound No. 2.2 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of active ingredient No. 2.2 are dissolved in a mixture which consists of 25 parts by weight of cyclohexanone, 65 parts by weight of a mineral oil fraction boiling within the range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. 2.2 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammermill. By finely distributing the mixture into 20,000 parts by weight of water, a spray liquor which contains 0.1% by weight of the active ingredient is obtained.

V. 3 parts by weight of active ingredient No. 2.2 are mixed with 97 parts by weight of finely divided kaolin. A dusting agent which contains 3% by weight of the active ingredient is obtained in this manner.

VI. 20 parts by weight of active ingredient No. 2.2 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The herbicides or the active ingredients can be applied by the preemergence or postemergence method. If the active ingredients are less well tolerated by certain crops, it is possible to use application methods in which the herbicides are sprayed with the aid of the sprayers so that the leaves of the sensitive crops are as far as possible not affected while the active ingredients reach the leaves of undesirable plants growing underneath or the uncovered soil surface (post-directed, lay-by).

The application rates of active ingredient are from 0.001 to 5, preferably from 0.01 to 2, kg/ha of active ingredient (a.i.), depending on the aim of control, the season, the target plants and the stage of growth.

In view of the versatility of the application methods, the novel compounds or the agents containing them can be used in a further number of crops for eliminating undesirable plants. Examples of suitable crops are the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Coffea arabica (Coffea canephora, Coffea liberica)* [sic], *Cucumis sativus, Cynodon dactylon, Daucus carota, Elaeis guineensis, Fragaria yesca, Glycine max, Gossypium hirsutum (Gossypium arboreum, Gossypium herbaceum, Gossypium vitifolium), Gossypium hirsutum (Gossypium arboreum, Gossypium herbaceum, Gossypium vitifolium), Gossypium hirsutum (Gossypium arborsum, Gossypium herbaceum, Gossypium vitifolium)* [sic], *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spp., *Manihot esculenta, Medicago sativa, Musa* spp., *Nicotiana tabacum (N. rustica), Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifoliumpratense, Triticum aestivum, Triticum durum, Vicia faba, Vitis vinifera, Zea mays.*

The compounds of the formula I can influence virtually all development stages of a plant in different ways and are therefore used as growth regulators. The diversity of action of the plant growth regulators depends in particular a) on the plant species and variety, b) on the time of application, based on the state of development of the plants and on the season c) on the place of application and application method (for example seed dressing, soil treatment, foliar application or trunk injection in the case of trees), d) on climatic factors, for example temperature and amount of precipitation, as well as length of day and light intensity, e) on the soil characteristics (including fertilizer application), f) on the formulation or application form of the active ingredient and finally g) on the concentration of active ingredient used.

From the many different potential applications of the plant growth regulators of the formula I in plant cultivation, in agriculture and in horticulture, some are mentioned below.

A.

With the compounds which can be used according to the invention, it is possible greatly to inhibit the vegetative growth of the plants, which is evident in particular from a reduction in the growth in length.

Accordingly, the treated plants exhibit stunted growth; moreover, a darker leaf coloration is observed.

A reduced intensity of the growth of grasses and crops susceptible to lodging, such as cereals, corn, sunflowers and soybean, proves advantageous in practice. Shortening and strengthening of the stems reduce or eliminate the danger of lodging of plants under unfavorable weather conditions prior to harvesting.

The use of growth regulators for inhibiting the growth in length and for changing the time of ripening in the case of cotton is also important. This permits completely mechanized harvesting of this important crop.

In the case of fruit trees and other trees, pruning costs can be saved by means of the growth regulators. Moreover, the alternation of fruit trees can be broken by means of growth regulators.

By using growth regulators, it is also possible to increase or inhibit the lateral branching of the plants. This is of interest when, for example in the case of tobacco plants, the formation of side shoots is to be inhibited in favor of foliar growth.

Growth regulators can also be used for considerably increasing the resistance to frost, for example in the case of winter rape. On the one hand, the growth in length and the development of foliage and plant mass which is too luxurious (and therefore particularly susceptible to frost) are inhibited. On the other hand, after sowing and prior to the onset of the winter frost, the young rape plants are held back in the vegetative stage of development in spite of favorable growth conditions. This also eliminates the danger of frost for plants which tend to exhibit premature cessation of inhibition of blooming and to grow over into the generative phase. In other crops too, for example winter cereals, it is advantageous if, through treatment with the novel compounds in the fall, the stocks are well tillered but do not start the winter with too luxurious a growth. A greater sensitivity to frost and—owing to the relatively small foliage or plant mass—attack by various diseases (for example fungal disease) can thus be prevented.

B.

The growth regulators can be used to achieve high yields of both plant parts and plant ingredients. For example, it is possible to induce the growth of larger amounts of buds, flowers, leaves, fruits, seed kernels, roots and tubers, to increase the content of sugar in sugarbeets, sugar cane and citrus fruits, to increase the protein content of cereals or soybean or to stimulate rubber trees to produce greater latex flow.

The compounds of the formula I can result in higher yields by intervening in the plant metabolism or by promoting or inhibiting vegetative and/or generative growth.

C.

Finally, plant growth regulators can be used both for shortening and lengthening the stages of development and for accelerating or slowing down the ripening of the harvested plant parts before or after harvesting.

For example, facilitating harvesting, which is made possible by concentrated dropping or a reduction in the adhesion to a tree in the case of citrus fruits, olives or other species and varieties of pomes, drupes and indehiscent fruit, is of commercial interest. The same mechanism, i.e. promotion of the formation of abscission tissue between fruit or leaf and stem part of the plant is also essential for readily controllable defoliation of crops such as cotton.

D.

The growth regulators can furthermore reduce the water consumption of plants. By using the novel substances, it is possible to reduce the intensity of irrigation and hence to carry out more economical farming because, inter alia, the extent of opening of the stomata is reduced,
a thicker epidermis and cuticle are formed,
the root penetration of the soil is improved and
the microclimate in the plant stock is favorably influenced by more compact growth.

Compounds I are particularly suitable for shortening the stems of crops such as barley, rape and wheat.

The active ingredients of the formula I which are to be used according to the invention can be fed to the crops both via the seed (as seed dressing) and via the soil, i.e. through the roots and—particularly preferably—via the foliage by spraying.

The application rate of active ingredient is not critical, owing to the high tolerance by plants. The optimum application rate varies depending on the aim of control, the season, the target plants and the stages of growth.

In the case of seed treatment, in general from 0.001 to 50, preferably from 0.01 to 10, g of active ingredient per kilogram of seed are required.

For foliage and soil treatment, in general doses of from 0.001 to 10, preferably from 0.01 to 3, in particular from 0.01 to 0.5, kg/ha are to be considered sufficient.

In order to broaden the action spectrum and to achieve synergistic effects, the compounds of the formula I may be mixed with many members of other groups of herbicidal or growth-regulating active ingredients and applied together with them. Suitable components of the mixture are, for example, diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives which carry, for example, a carboxyl or carbimino group in the 2 position, quinoline carboxylic acid derivatives, imidazolinones, sulfonamides, sulfonylureas, aryloxy- and heteroaryloxyphenoxypropionic acids and their salts, esters and amides and others.

It may also be useful to apply the compounds of the formula I, alone or in combination with other herbicides, also as a mixture with further crop protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates may also be added.

Synthesis examples

Synthesis of compounds of the general formula VI

EXAMPLE 1

Methyl 3-phenoxy-3-phenyl-2-hydroxybutyrate 28.2 g (0.3 mol) of phenol and 19.2 g (0.1 mol) of methyl 3-phenyl-2,3-epoxybutyrate are heated together for 6 hours at 100° C. After the excess phenol has been distilled off under greatly reduced pressure and the residue has been purified by chromatography over silica gel using a hexane/ethyl acetate mixture, 17.9 g of a slightly yellow oil are obtained.

Yield: 62.5%

EXAMPLE 2

Methyl 3-(4-bromophenoxy)-3-phenyl-2-hydroxybutyrate 51.9 g (0.3 mol) of 4-bromophenol and 19.2 g (0.1 mol) of methyl 3-phenyl-2,3-epoxybutyrate are stirred for 8 hours at 100° C. and for 12 hours at room temperature. After the excess phenol has been distilled off, the residue is purified by flash chromatography (silica gel, 9:1 n-hexane/ethyl acetate). 7.2 g of a white solid are obtained.

Yield: 20%

Mp.: 133°–135° C.

The compounds stated in Table 1 are prepared similarly:

TABLE 1

Intermediates of the formula VIa where $R^1$ is $CH_3$ $$R^6-O-\underset{R^5}{\underset{|}{C}}-\underset{COOCH_3}{\underset{|}{CH}}-OH \quad \text{with } R^4 \text{ on } C$$

| | $R^6$ | $R^4$ | $R^5$ | Mp. [°C.] |
|---|---|---|---|---|
| 1.1 | Phenyl | Phenyl | Methyl | oil |
| 1.2 | 4-Bromophenyl | Phenyl | Methyl | 130–133 |
| 1.3 | Phenyl | Methyl | Methyl | |
| 1.4 | Phenyl | Phenyl | i-Propyl | |
| 1.5 | 2-Fluorophenyl | Phenyl | Methyl | |
| 1.6 | 3-Fluorophenyl | Phenyl | Methyl | oil |
| 1.7 | 4-Fluorophenyl | Phenyl | Methyl | oil |
| 1.8 | 4-Chlorophenyl | Phenyl | Methyl | |
| 1.9 | 4-Nitrophenyl | Phenyl | Methyl | |
| 1.10 | 4-Methylphenyl | Phenyl | Methyl | oil |
| 1.11 | Phenyl | 2-Fluorophenyl | Methyl | |
| 1.12 | Phenyl | 3-Methoxyphenyl | Methyl | |
| 1.13 | Phenyl | 4-i-Propylphenyl | Methyl | |
| 1.14 | Phenyl | 2-Methylphenyl | Methyl | |
| 1.15 | Phenyl | 3-Nitrophenyl | Methyl | |

TABLE 1-continued

Intermediates of the formula VIa where $R^1$ is $CH_3$ $$R^6-O-\underset{\underset{COOCH_3}{|}}{\overset{\overset{R^4}{|}}{C}}-CH-OH$$
$$\phantom{R^6-O-}\underset{R^5}{|}$$

| | $R^6$ | $R^4$ | $R^5$ | Mp. [°C.] |
|---|---|---|---|---|
| 1.16 | Phenyl | 4-Bromophenyl | Methyl | |
| 1.17 | Phenyl | 2-Furyl | Methyl | |
| 1.18 | Phenyl | 2-Thienyl | Methyl | oil |
| 1.19 | Phenyl | 3-Furyl | Methyl | |
| 1.20 | Phenyl | 3-Thienyl | Methyl | |
| 1.21 | 3-Methylphenyl | Phenyl | Methyl | oil |
| 1.22 | 2-Methylphenyl | Phenyl | Methyl | oil |
| 1.23 | 4-i-Propylphenyl | Phenyl | Methyl | oil |
| 1.24 | Phenyl | 4-Chlorophenyl | Methyl | oil |

Synthesis of compounds of the general formula I:

EXAMPLE 3

Methyl 3-phenoxy-3-phenyl-2-(4,6-dimethoxypyrimidin-2-yloxy)butyrate 4.4 g (15.4 mmol) of methyl 3-phenoxy-3-phenyl-2-hydroxybutyrate (compound 1.1) are dissolved in 40 ml of dimethylformamide, and 0.46 g (18.4 mmol) of sodium hydride are added. Stirring is carried out for 1 hour, after which 3.4 g (15.4 mmol) of 4,6-dimethoxy-2-methylsulfonylpyrimidine are added. After stirring has been carried out for 24 hours at room temperature, hydrolysis is effected carefully with 10 ml of water, the pH is brought to 5 with acetic acid and the solvent is distilled off under greatly reduced pressure. The residue is taken up in 100 ml of ethyl acetate, washed with water and dried over sodium sulfate and the solvent is distilled off. 10 ml of methyl tert-butyl ether are added to the residue and the precipitate formed is filtered off with suction. After drying, 1.6 g of a white powder remains.

Yield: 24.5%

Mp.: 143°–145° C.

EXAMPLE 4

3-Phenoxy-3-phenyl-2-(4,6-dimethoxypyrimidin-2-yloxy)butyrate 1.3 g of methyl 3-phenoxy-3-phenyl-2-(4,6-dimethoxypyrimidin-2-yloxy)butyrate (Example 3) are dissolved in 20 ml of methanol and 40 ml of tetrahydrofuran, and 3.7 g of 10% strength NaOH solution are added. Stirring is carried out for 6 hours at 60° C. and for 12 hours at room temperature, the solvent is distilled off under reduced pressure and the residue is taken up in 100 ml of water. Unconverted ester is extracted with ethyl acetate. The aqueous phase is then brought to pH 1–2 with dilute hydrochloric acid and is extracted with ethyl acetate. After drying has been carried out over magnesium sulfate and the solvent has been distilled off, 1.0 g of a white powder remain [sic].

Yield: 79.7%

Mp.: 50°–55° C.

EXAMPLE 5

Methyl 3-phenoxy-3-phenyl-2-(4,6-dimethoxypyrmidin-2-ylthio)butyrate [sic]

7.2 g (25 mmol) of methyl 3-phenoxy-3-phenyl-2-hydroxybutyrate (compound 1.1) are dissolved in 50 ml of dichloromethane, 3 g (30 mmol) of triethylamine are added and 3.2 g (28 mmol) of methanesulfonyl chloride are added dropwise while stirring. Stirring is continued for 2 hours at room temperature, and the mixture is washed with water, dried over magnesium sulfate and evaporated down under reduced pressure. The residue is taken up in 100 ml of dimethylformamide and the solution is added dropwise at 0° C. to a suspension of 12.9 g (75 mmol) of 4,6-dimethoxpyrimidine-2-thiol [sic] and 8.4 g (100 mmol) of sodium bicarbonate in 100 ml of dimethylformamide. After stirring has been carried out for 2 hours at room temperature and for a further 2 hours at 60° C., the mixture is poured onto 1 l of ice water and the resulting precipitate is filtered off with suction. After drying, 4.2 g of a white powder remain.

Yield: 38%

The compounds stated in Table 2 were prepared similarly to the above examples.

TABLE 2

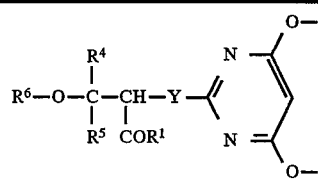

| Ex. No. | $R^6$ | $R^4$ | $R^5$ | $R^1$ | Y | Mp. [°C.] |
|---|---|---|---|---|---|---|
| 2.1 | Phenyl | Phenyl | Methyl | $OCH_3$ | O | 100–103 |
| 2.2 | Phenyl | Phenyl | Methyl | OH | O | 50–55 |
| 2.3 | Phenyl | Phenyl | Methyl | $OCH_3$ | S | |
| 2.4 | Phenyl | Phenyl | Methyl | OH | S | |
| 2.5 | Phenyl | Phenyl | i-Propyl | $OCH_3$ | O | |
| 2.6 | Phenyl | Phenyl | i-Propyl | OH | O | |
| 2.7 | Phenyl | Methyl | Methyl | $OCH_3$ | O | |
| 2.8 | Phenyl | Methyl | Methyl | OH | O | |
| 2.9 | 4-Bromophenyl | Phenyl | Methyl | $OCH_3$ | O | 130–135 |
| 2.10 | 4-Bromophenyl | Phenyl | Methyl | OH | O | 155–160 |
| 2.11 | 2-Fluorophenyl | Phenyl | Methyl | $OCH_3$ | O | 128–134 |
| 2.12 | 2-Fluorophenyl | Phenyl | Methyl | OH | O | 170–171 |
| 2.13 | 3-Fluorophenyl | Phenyl | Methyl | $OCH_3$ | O | 85–90 |

TABLE 2-continued $$R^6-O-\underset{\underset{COR^1}{|}}{\overset{\overset{R^4}{|}}{C}}-CH-Y-\left\langle\begin{array}{c}N\\ \\ N\end{array}\right.\begin{array}{c}O-\\ \\ O-\end{array}$$

| Ex. No. | R⁶ | R⁴ | R⁵ | R¹ | Y | Mp. [°C.] |
|---|---|---|---|---|---|---|
| 2.14 | 3-Fluorophenyl | Phenyl | Methyl | OH | O | 167–169 |
| 2.15 | 4-Fluorophenyl | Phenyl | Methyl | OCH₃ | O | 115–116 |
| 2.16 | 4-Fluorophenyl | Phenyl | Methyl | OH | O | 122–125 |
| 2.17 | 4-Chlorophenyl | Phenyl | Methyl | OCH₃ | O | oil |
| 2.18 | 4-Chlorophenyl | Phenyl | Methyl | OH | O | 94–98 |
| 2.19 | 4-Methylphenyl | Phenyl | Methyl | OCH₃ | O | 100–114 |
| 2.20 | 4-Methylphenyl | Phenyl | Methyl | OH | O | oil |
| 2.21 | 4-Nitrophenyl | Phenyl | Methyl | OCH₃ | O | |
| 2.22 | 4-Nitrophenyl | Phenyl | Methyl | OH | O | |
| 2.23 | Phenyl | 2-Fluorophenyl | Methyl | OCH₃ | O | 130–132 |
| 2.24 | Phenyl | 2-Fluorophenyl | Methyl | OH | O | 194–195 |
| 2.25 | Phenyl | 3-Methoxyphenyl | Methyl | OCH₃ | O | oil |
| 2.26 | Phenyl | 3-Methoxyphenyl | Methyl | OH | O | oil |
| 2.27 | Phenyl | 4-i-Propylphenyl | Methyl | OCH₃ | O | |
| 2.28 | Phenyl | 4-i-Propylphenyl | Methyl | OH | O | |
| 2.29 | Phenyl | 4-Bromophenyl | Methyl | OCH₃ | O | 129–131 |
| 2.30 | Phenyl | 4-Bromophenyl | Methyl | OH | O | oil |
| 2.31 | Phenyl | 2-Furyl | Methyl | OCH₃ | O | |
| 2.32 | Phenyl | 2-Furyl | Methyl | OH | O | |
| 2.33 | Phenyl | 3-Furyl | Methyl | OCH₃ | O | |
| 2.34 | Phenyl | 3-Furyl | Methyl | OH | O | |
| 2.35 | Phenyl | 2-Thienyl | Methyl | OCH₃ | O | |
| 2.36 | Phenyl | 2-Thienyl | Methyl | OH | O | |
| 2.37 | Phenyl | 3-Thienyl | Methyl | OCH₃ | O | |
| 2.38 | Phenyl | 3-Thienyl | Methyl | OH | O | |
| 2.39 | 3-Methylphenyl | Phenyl | Methyl | OCH₃ | O | 155 |
| 2.40 | 3-Methylphenyl | Phenyl | Methyl | OH | O | 100–101 |
| 2.41 | 4-i-Propylphenyl | Phenyl | Methyl | OCH₃ | O | 130–131 |
| 2.42 | 4-i-Propylphenyl | Phenyl | Methyl | OH | O | 230 |
| 2.43 | Phenyl | 4-Chlorophenyl | Methyl | OCH₃ | O | 143–144 |
| 2.44 | Phenyl | 4-Chlorophenyl | Methyl | OH | O | 90–92 |
| 2.45 | Phenyl | 2-Methylphenyl | Methyl | OCH₃ | O | 179–180 |
| 2.46 | Phenyl | 2-Methylphenyl | Methyl | OH | O | |
| 2.47 | 2-Methylphenyl | Phenyl | Methyl | OCH₃ | O | 95–114 |
| 2.48 | 2-Methylphenyl | Phenyl | Methyl | OH | O | 80–85 |
| 2.49 | Phenyl | 4-Methylphenyl | Methyl | OCH₃ | O | 110–112 |
| 2.50 | Phenyl | 4-Methylphenyl | Methyl | OH | O | 156–157 |
| 2.51 | Phenyl | 3-Methylphenyl | Methyl | OCH₃ | O | oil |
| 2.52 | Phenyl | 3-Methylphenyl | Methyl | OH | O | 158–160 |
| 2.53 | 4-Methoxyphenyl | Phenyl | Methyl | OCH₃ | O | 157–158 |
| 2.54 | 4-Methoxyphenyl | Phenyl | Methyl | OH | O | 106–107 |
| 2.55 | Phenyl | 4-Fluorophenyl | Methyl | OCH₃ | O | 160–165 |
| 2.56 | Phenyl | 4-Fluorophenyl | Methyl | OH | O | 99–100 |
| 2.57 | 4-Methylthiophenyl | Phenyl | Methyl | OCH₃ | O | 160–163 |
| 2.58 | 4-Methylthiophenyl | Phenyl | Methyl | OH | O | 248–250 |
| 2.59 | 4-t-Butylphenyl | Phenyl | Methyl | OCH₃ | O | 106–110 |
| 2.60 | 4-t-Butylphenyl | Phenyl | Methyl | OH | O | 250 |
| 2.61 | Phenyl | Phenyl | Ethyl | OCH₃ | O | 115–117 |
| 2.62 | Phenyl | Phenyl | Ethyl | OH | O | 84–85 |
| 2.63 | 4-Acetoxyphenyl | Phenyl | Methyl | OCH₃ | O | 157–159 |
| 2.64 | 4-Hydroxyphenyl | Phenyl | Methyl | OH | O | 80–90 |

Use examples:

a) Herbicidal action

The herbicidal action of the 3-(het)aryloxy(thio)carboxylic acid derivatives of the formula I is demonstrated by the following greenhouse experiments:

The culture vessels used were plastic flowerpots containing loamy sand with about 3.0% of humus as a substrate. The seeds of the test plant were sown separately according to species.

In the preemergence treatment, the active ingredients suspended or emulsified in water were applied directly after sowing by means of finely distributing nozzles. The vessels were lightly sprinkler-irrigated in order to promote germination and growth and were then covered with transparent plastic covers until the plants had begun to grow. This covering ensures uniform germination of the test plants, unless this has been adversely affected by the active ingredients.

For the postemergence treatment, the test plants are grown to a height of growth of from 3 to 15 cm, depending on the form of growth, before being treated with the active ingredients suspended or emulsified in water. For this purpose, the test plants are either sown directly and grown in the same vessels or first grown separately as seedlings and transplanted into the test vessels a few days before the treatment.

The application rate for the postemergence treatment is 0.5 or 0.25 kg/ha of a.i. (active ingredient).

The plants were kept at 10°–25° C. or 20°–35° C., according to species. The experimental period is extended over from 2 to 4 weeks. During this time, the plants were tended and their reaction to the individual treatments was evaluated.

Evaluation was based on a scale from 0 to 100. 100 means no emergence of the plant or complete destruction of at least the above-ground parts and 0 means no damage or normal course of growth.

The plants used in the greenhouse experiments consist of the following species:
Botanical Name

*Amaranthus retroflexus*

*Polygonumpersicaria*

*Solanum nigrum*

Common Name redroot pigweed redshank black nightshade

Broad-leaved undesirable plants can be very readily controlled with Example No. 2.2 when used at 0.5 and 0.25 kg/ha a.i. by the postemergence method.

b) Bioregulatory action

The growth-regulating action of the 3-(het)aryloxy(thio) carboxylic acid derivatives of the formula I is determined by length measurement, the growth and treatment of the test plants being carried out as described above. Experiments were evaluated by expressing the height of growth of the treated plants in relation to the height of growth of untreated plants.

The experimental results are listed in Tables 3–7 below.

TABLE 3

Summer wheat Ralle, postemergence foliar treatment

| Example No. | Dose kg/ha | Relative heights of growth |
|---|---|---|
| untreated | — | 100 |
| 2.17 | 0.1 | 88 |
| 2.19 | 0.1 | 94 |
| 2.64 | 0.1 | 89 |
| 2.59 | 0.5 | 76 |
| 2.55 | 0.5 | 82 |
| 2.50 | 0.5 | 89 |
| 2.62 | 0.5 | 78 |
| 2.60 | 0.5 | 83 |
| 2.61 | 0.5 | 81 |
| 2.56 | 0.5 | 77 |

TABLE 4

Summer wheat Ralle, postemergence foliar treatment

| Example No. | Dose kg/ha | Relative heights of growth |
|---|---|---|
| untreated | — | 100 |
| 2.26 | 1.5 | 85 |
|  | 0.75 | 92 |
|  | 0.375 | 98 |
|  | 0.1875 | 100 |
| 2.30 | 1.5 | 70 |
|  | 0.75 | 79 |
|  | 0.375 | 91 |
|  | 0.1875 | — |
| 2.54 | 1.5 | 49 |

TABLE 4-continued

Summer wheat Ralle, postemergence foliar treatment

| Example No. | Dose kg/ha | Relative heights of growth |
|---|---|---|
|  | 0.75 | 64 |
|  | 0.375 | 70 |
|  | 0.1875 | 94 |
| 2.58 | 1.5 | 64 |
|  | 0.75 | 76 |
|  | 0.375 | 76 |
|  | 0.1875 | 94 |
| 2.57 | 1.5 | 67 |
|  | 0.75 | 67 |
|  | 0.375 | 79 |
|  | 0.1875 | 85 |
| 2.59 | 1.5 | 40 |
|  | 0.75 | 40 |
|  | 0.375 | 79 |
|  | 0.1875 | 88 |
| 2.62 | 1.5 | 73 |
|  | 0.75 | 73 |
|  | 0.375 | 79 |
|  | 0.1875 | 92 |
| 2.60 | 1.5 | 85 |
|  | 0.75 | 89 |
|  | 0.375 | 95 |
|  | 0.1875 | 100 |

TABLE 5

Summer barley Alexis, postemergence foliar treatment

| Example No. | Dose kg/ha | Relative heights of growth |
|---|---|---|
| untreated | — | 100 |
| 2.26 | 0.75 | 83 |
|  | 0.375 | 86 |
|  | 0.1875 | 96 |
|  | 0.0937 | 96 |
| 2.30 | 1.5 | 63 |
|  | 0.75 | 70 |
|  | 0.375 | 83 |
|  | 0.1875 | — |
| 2.54 | 1.5 | 43 |
|  | 0.75 | 53 |
|  | 0.375 | 66 |
|  | 0.1875 | 86 |
| 2.58 | 1.5 | 76 |
|  | 0.75 | 80 |
|  | 0.375 | 100 |
|  | 0.1875 | — |
| 2.57 | 1.5 | 60 |
|  | 0.75 | 86 |
|  | 0.375 | 86 |
|  | 0.1875 | 86 |
| 2.59 | 1.5 | 70 |
|  | 0.75 | 80 |
|  | 0.375 | 90 |
|  | 0.1875 | 93 |
| 2.62 | 1.5 | 73 |
|  | 0.75 | 83 |
|  | 0.375 | 83 |
|  | 0.1875 | 87 |
| 2.42 | 0.5 | 84 |
|  | 0.25 | 89 |
|  | 0.125 | 95 |
|  | 0.0625 | — |
| 2.59 | 0.5 | 86 |
|  | 0.25 | 95 |
|  | 0.125 | 95 |
|  | 0.0625 | 95 |

TABLE 6

Summer rape Petranova, postemergence foliar treatment

| Example No. | Dose kg/ha | Relative heights of growth |
|---|---|---|
| untreated | — | 100 |
| 2.17 | 0.1 | 74 |
| 2.19 | 0.1 | 77 |
| 2.39 | 0.1 | 77 |
| 2.63 | 0.1 | 92 |
| 2.64 | 0.1 | 90 |
| 2.51 | 0.5 | 69 |
| 2.23 | 0.5 | 69 |
| 2.43 | 0.5 | 66 |
| 2.53 | 0.5 | 69 |
| 2.44 | 0.5 | 69 |
| 2.57 | 0.5 | 83 |
| 2.55 | 0.5 | 60 |
| 2.50 | 0.5 | 72 |
| 2.62 | 0.5 | 81 |
| 2.60 | 0.5 | 72 |
| 2.61 | 0.5 | 96 |
| 2.56 | 0.5 | 87 |

TABLE 5

Summer barley Alexis, postemergence foliar treatment

| Example No. | Dose kg/ha | Relative heights of growth |
|---|---|---|
| untreated | — | 100 |
| 2.26 | 0.75 | 57 |
|  | 0.375 | 66 |
|  | 0.1875 | 66 |
|  | 0.0937 | 66 |
| 2.30 | 1.5 | — |
|  | 0.75 | — |
|  | 0.375 | 58 |
|  | 0.1875 | 64 |
| 2.54 | 1.5 | 79 |
|  | 0.75 | 79 |
|  | 0.375 | 90 |
|  | 0.1875 | 90 |
| 2.58 | 1.5 | 85 |
|  | 0.75 | — |
|  | 0.375 | 85 |
|  | 0.1875 | 85 |
| 2.42 | 0.5 | 55 |
|  | 0.25 | 55 |
|  | 0.125 | 68 |
|  | 0.0625 | 68 |
| 2.59 | 0.5 | 79 |
|  | 0.25 | 79 |
|  | 0.125 | 84 |
|  | 0.0625 | 84 |

We claim:

1. A 3-(het)aryloxy(thio)carboxylic acid derivative of the formula I where
$R^1$ is
  (a) hydrogen;
  (b) a succinylimidoxy group;
  (c) a 5-membered heteroaromatic structure which is bonded via a nitrogen atom, contains two or three nitrogen atoms and may carry one or two halogen atoms or one or two of the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
  (d) a radical $$-(O)_m N \begin{matrix} R^7 \\ R^8 \end{matrix}$$

where m is 0 or 1 and $R^7$ and $R^8$, which may be identical or different, have the following meanings: hydrogen;
  $C_1$–$C_8$-alkyl, $C_3$–$C_6$-alkenyl, $C_3$–$C_6$-alkynyl or $C_3$–$C_{12}$-cycloalkyl, where each of these radicals may carry one to five halogen atoms or one or two of the following groups:
  $C_1$–$C_4$-alkoxy, $C_3$–$C_6$-alkenyloxy, $C_3$–$C_6$-alkynyloxy, $C_1$–$C_4$-alkylthio, $C_3$–$C_6$-alkenylthio, $C_3$–$C_6$-alkynylthio, $C_1$–$C_4$-haloalkoxy, $C_1$–$C_6$-alkylcarbonyl, $C_3$–$C_6$-alkenylcarbonyl, $C_3$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, di-$C_1$–$C_4$-alkylamino, cyclo-$C_1$–$C_6$-alkyl, phenyl or phenyl which is monosubstituted or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
  phenyl which may be substituted by one or more of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
  $R^7$ and $R^8$ together form a cyclic, optionally substituted $C_4$–$C_7$-alkylene chain or together form a cyclic, optionally substituted $C_3$–$C_6$-alkylene chain containing a heteroatom selected from the group consisting of oxygen, sulfur and nitrogen;
  (e) $R^1$ is furthermore a group $$-O-(CH_2)_p - \overset{(O)_k}{\underset{\|}{S}} - R^9$$

where $R^9$ is $C_1$–$C_4$-alkyl, phenyl or phenyl which is mono-substituted or polysubstituted by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-akylthio, or $C_1$–$C_4$-haloalkyl, $C_3$–$C_6$-alkenyl or $C_3$–$C_6$-alkynyl, p may be 1, 2, 3 or 4 and k may be 0, 1 or 2,
  (f) a radical $OR^{10}$, where $R^{10}$ is:
  i) hydrogen, an alkali metal cation, one equivalent of an alkaline earth metal cation, the ammonium cation or an organic ammonium ion;
  ii) $C_3$–$C_{12}$-cycloalkyl which may carry one to three $C_1$–$C_4$-alkyl radicals;
  iii) $C_1$–$C_{10}$-alkyl which may carry one to five halogen atoms or one of the following radicals:
    $C_1$–$C_4$-alkoxy, $C_1$–$C_4$-alkylthio, cyano, $C_1$–$C_8$-alkylcarbonyl, $C_3$–$C_{12}$-cycloalkyl, $C_1$–$C_8$-alkoxycarbonyl, phenyl, phenoxy or phenylcarbonyl, where the aromatic radicals in turn may each carry one to five halogen atoms or one to three of the following radicals:
    $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;
  iv) $C_1$–$C_{10}$-alkyl which may carry one to five halogen atoms and carries one of the following radicals: a 5-membered heteroaromatic structure containing one to three nitrogen atoms or a 5-membered heteroaromatic structure containing one nitrogen atom and one oxygen or sulfur atom, each of its structures may carry one to four halogen atoms or one or two of the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

v) $C_2$–$C_6$-alkyl which carries one of the following radicals in the 2 position: $C_1$–$C_6$-alkoxyimino, $C_3$–$C_6$-alkenyloxyimino, $C_3$–$C_6$-haloalkenyloxyimino or benzyloxyimino;

vi) $C_3$–$C_6$-alkenyl or $C_3$–$C_6$-alkynyl, where these groups in turn may carry one to five halogen atoms;

vii) phenyl which may carry one to five halogen atoms or one to three of the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-akylthio;

viii) a 5-membered heteroaromatic structure which has bonded via a nitrogen atom, contains one to three nitrogen atoms and may carry one or two halogen atoms or one or two of the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

ix) a group

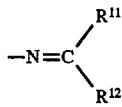

where $R^{11}$ and $R^{12}$, may be identical or different and are each:

$C_1$–$C_{10}$-alkyl, $C_3$–$C_6$-alkenyl, $C_3$–$C_6$-alkynyl or $C_3$–$C_7$-cycloalkyl, where these radicals may carry one $C_1$–$C_4$-alkoxy or $C_1$–$C_4$-alkylthio or one phenyl radical;

phenyl which may be substituted by one or more of the following radicals:
halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

or $R^{11}$ and $R^{12}$ together form a $C_3$–$C_{12}$-alkylene chain which may carry one to three $C_1$–$C_4$-alkyl groups;

(g) or $R^1$ forms a radical

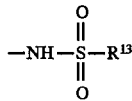

where $R^{13}$ is:
$C_1$–$C_4$-alkyl, $C_3$–$C_6$-alkenyl, $C_3$–$C_6$-alkynyl or $C_3$–$C_7$-cycloalkyl, where these radicals may carry one $C_1$–$C_4$-alkoxy or $C_1$–$C_4$-alkylthio or one phenyl radical;

phenyl which may be substituted by one to five halogen atoms or by one to three of the following radicals: halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

$R^2$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

X is nitrogen or $CR^{14}$, where $R^{14}$ is hydrogen or, together with $R^3$, forms a 3-membered or 4-membered alkylene or alkenylene chain, in each of which a methylene group is replaced by oxygen;

$R^3$ is halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio or $R^3$ is linked to $R^{14}$ as stated above to form a 5-membered or 6-membered ring;

$R^4$ is $C_1$–$C_{10}$-alkyl which may carry one to five halogen atoms or one of the following radicals: $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl, where the phenyl radicals in turn may carry one to five halogen atoms or one to three of the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

$C_1$–$C_{10}$-alkyl which may carry one to five halogen atoms and carries one of the following radicals: a five-membered heteroaromatic structure which contains one to three nitrogen atoms or one sulfur or oxygen atom and may carry one to four halogen atoms or one or two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or phenyl;

a $C_3$–$C_{12}$-cycloalkyl or $C_3$–$C_{12}$-cycloalkenyl group which may contain one oxygen or sulfur atom and may carry one to five halogen atoms or one of the following radicals: $C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl, where the phenyl radicals in turn may carry one to five halogen atoms or one to three of the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

$C_3$–$C_6$-alkenyl or $C_3$–$C_6$-alkynyl, each of which may carry one to five halogen atoms or one of the following radicals: $C_1$–$C_4$-alkyl, $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl, where the phenyl radicals in turn may carry one to five halogen atoms or one to three of the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

a five-membered or six-membered heteroaromatic structure which contains one to three nitrogen atoms or one sulfur or oxygen atom and may carry one to four halogen atoms or one or two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl, phenoxy or phenylcarbonyl, where the phenyl radicals in turn may carry one to five halogen atoms or one to three of the following radicals:
$C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

phenyl or naphthyl, each of which may be substituted by one or more of the following radicals: halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, amino, $C_1$–$C_4$-alkylamino or $C_1$–$C_4$-dialkylamino;

$R^4$ and $R^5$, together with the neighboring carbon atom, form a 3-membered to 8-membered ring which may contain one oxygen or sulfur atom and may carry one to three of the following radicals: $C_1$–$C_4$-alkyl, halogen, $C_1$–$C_4$-haloalkyl, $C_1$–$C_4$-alkoxy, $C_1$–$C_4$-haloalkoxy or $C_1$–$C_4$-alkylthio;

$R^5$ is hydrogen, $C_1$–$C_4$-alkyl, $C_3$–$C_6$-alkenyl, $C_3$–$C_6$-alkynyl, $C_3$–$C_7$-cycloalkyl, $C_1$–$C_4$-haloalkyl, $C_1$–$C_4$- alkoxyalkyl, $C_1$-$C_4$-alkylthioalkyl or phenyl or $R^5$ is linked to $R^4$ as stated above to form a 3-membered to 8-membered ring;

$R^6$ is phenyl or naphthyl, each of which may be substituted by one or more of the following radicals: halogen, nitro, cyano, hydroxyl, amino, $C_1$-$C_4$-alkyl, $C_1$-$C_4$-haloalkyl, $C_1$-$C_4$-alkoxy, $C_1$-$C_4$-haloalkoxy, phenoxy, $C_1$-$C_4$-alkylthio, $C_1$-$C_4$-alkylamino or $C_1$-$C_4$-dialkylamino;

a five-membered or six-membered hetehoaromatic structure which contains one to three nitrogen atoms or one sulfur or oxygen atom and may carry one to four halogen atoms or one or two of the following radicals: $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, phenyl, phenoxy or phenylcarbonyl, where the phenyl radicals in turn may carry one to five halogen atoms or one to three of the following radicals: $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio;

Y is sulfur or oxygen or a single bond; and

Z is sulfur or oxygen.

2. An aryloxycarboxylic acid derivative of the formula I as claimed in claim 1, in which Z is oxygen, $R^6$ is phenyl which may be substituted as stated in claim 1 and $R^1$ to $R^5$, X and Y have the meanings stated in claim 1.

3. A (het)aryloxycarboxylic acid derivative of the formula I as claimed in claim 1, in which Y and Z are each oxygen, X is CH, $R^2$ and $R^3$ are each methoxy and $R^1$, $R^4$, $R^5$ and $R^6$ have the meanings stated in claim 1.

4. An aryloxycarboxylic acid derivative of the formula I as claimed in claim 1, in which Z is oxygen, X is CH, $R^2$ and $R^3$ are each methoxy, $R^6$ is phenyl which may be substituted as stated in claim 1 and $R^1$, $R^4$, $R^5$ and X have the meanings stated in claim 1.

5. An aryloxycarboxylic acid derivative of the formula I as claimed in claim 1, in which Y and Z are each oxygen, X is CH, $R^2$ and $R^3$ are each methoxy, $R^5$ is methyl, $R^4$ and $R^6$ are each phenyl which may be substituted as stated in claim 1 and $R^1$ has the meanings stated in claim 1.

6. An aryloxycarboxylic acid derivative of the formula I as claimed in claim 1, in which Y and Z are each oxygen, X is CH, $R^2$ and $R^3$ are each methoxy, $R^5$ is $C_1$-$C_4$-alkyl, $R^4$ and $R^6$ are each phenyl which may be substituted as stated in claim 1, $R^1$ is $OR^{10}$ and $R^{10}$ has the meanings stated in claim 1.

7. An aryloxycarboxylic acid derivative of the formula I as claimed in claim 1, in which $R^1$ is $OR^{10}$ and $R^{10}$ is hydrogen or $C_1$-$C_4$-alkoxy.

8. A herbicide containing a compound of the formula I as claimed in claim 1 and conventional inert additives.

9. A method for controlling undesirable plant growth, wherein a herbicidal amount of a compound of the formula I as claimed in claim 1 is allowed to act on the plants or on their habitat.

10. An agent for influencing plant growth, containing a compound of the formula I as claimed in claim 1 and conventional inert additives.

11. A method for regulating plant growth, wherein a bioregulatory amount of a compound of the formula I as claimed in claim 1 is allowed to act on the plants or on their habitat.

12. A process for the preparation of a 3-(het)aryloxy(thio) carboxylic acid derivative of the formula I as claimed in claim 1, where Y is oxygen, wherein a 3-(het)aryloxy(thio) carboxylic acid derivative of the formula VI

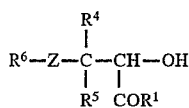

where $R^1$, $R^4$, $R^5$, $R^6$ and Z have the meanings stated in claim 1, is reacted with a compound of the formula VII

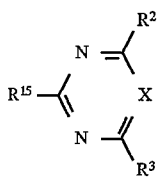

where $R^{15}$ is halogen or $R^{16}SO_2$— and $R^{16}$ is $C_1$-$C_4$-alkyl, $C_1$-$C_4$-haloalkyl or phenyl, in an inert solvent with the addition of a base.

13. A process for the preparation of a 3-(het)aryloxy(thio)-carboxylic acid derivative of the formula I as claimed in claim 1, where Y is sulfur, wherein a 3-(het)aryloxy(thio) carboxylic acid derivative of the formula VIII

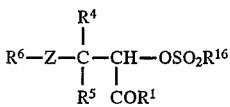

where $R^1$, $R^4$, $R^5$, $R^6$ and Z have the meanings stated in claim 1 and $R^{16}$ is $C_1$-$C_4$-alkyl, $C_1$-$C_4$-haloalkyl or phenyl is reacted with a compound of the formula IX

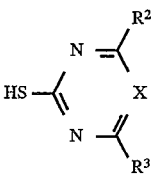

where the substituents have the meanings stated in claim 1.

14. A process for the preparation of a 3-(het)aryloxy(thio) carboxylic acid derivative of the formula I as claimed in claim 1, where Y is sulfur, wherein a 3-(het)aryloxy(thio) carboxylic acid derivative of the formula VIII

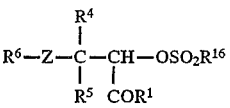

where $R^1$, $R^4$, $R^5$, $R^6$ and Z have the means stated in claim 1 and $R^{16}$ is $C_1$-$C_4$-alkyl, $C_1$-$C_4$-haloalkyl or phenyl is reacted with a compound of the formula IX

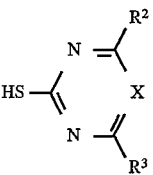

where the substituents have the meanings stated in claim 1.

* * * * *